(12) United States Patent
Kwon et al.

(10) Patent No.: US 9,901,422 B2
(45) Date of Patent: Feb. 27, 2018

(54) DENTAL WIRE SUPPORTER FOR ORTHODONTIC TREATMENT AND ORTHODONTIC DEVICE HAVING THE SAME

(71) Applicants: Soon Yong Kwon, Seoul (KR); Ji Min Kwon, Seoul (KR); Yong Min Kwon, Seoul (KR)

(72) Inventors: Soon Yong Kwon, Seoul (KR); Ji Min Kwon, Seoul (KR); Yong Min Kwon, Seoul (KR)

( * ) Notice: Subject to any disclaimer, the term of this patent is extended or adjusted under 35 U.S.C. 154(b) by 0 days.

(21) Appl. No.: 15/069,980

(22) Filed: Mar. 15, 2016

(65) Prior Publication Data
US 2016/0270885 A1  Sep. 22, 2016

(30) Foreign Application Priority Data
Mar. 16, 2015  (KR) .................. 10-2015-0035913

(51) Int. Cl.
*A61C 7/28*  (2006.01)
*A61C 7/22*  (2006.01)

(52) U.S. Cl.
CPC .............. *A61C 7/282* (2013.01); *A61C 7/22* (2013.01)

(58) Field of Classification Search
CPC .................................. A61C 7/282; A61C 7/22
USPC ..................................................... 433/16, 17
See application file for complete search history.

(56) References Cited

U.S. PATENT DOCUMENTS

| | | | | |
|---|---|---|---|---|
| 3,302,288 A | * | 2/1967 | Tepper | A61C 7/282 433/17 |
| 3,335,496 A | * | 8/1967 | Andrews | A61C 7/282 433/17 |
| 3,494,034 A | * | 2/1970 | Kesling | A61C 7/282 433/17 |
| 3,815,238 A | * | 6/1974 | Wallshein | A61C 7/282 433/17 |
| 3,874,080 A | * | 4/1975 | Wallshein | A61C 7/282 433/16 |
| 4,424,031 A | * | 1/1984 | Dahan | A61C 7/00 433/17 |
| 4,897,035 A | * | 1/1990 | Green | A61C 7/282 433/17 |
| 5,320,526 A | * | 6/1994 | Tuneberg | A61C 7/282 433/16 |
| 5,538,422 A | * | 7/1996 | Arndt | A61C 7/00 433/17 |
| 5,931,667 A | * | 8/1999 | Papandreas | A61C 7/12 433/10 |
| 6,004,131 A | * | 12/1999 | Lazzara, Jr. | A61C 7/282 433/17 |
| 6,039,564 A | * | 3/2000 | Hendrick | A61C 7/12 433/17 |

(Continued)

*Primary Examiner* — Nicholas Lucchesi
(74) *Attorney, Agent, or Firm* — Park, Kim & Suh, LLC

(57) ABSTRACT

Disclosed are a dental wire supporter, which supports an orthodontic wire and limits the movement of the orthodontic wire in a predetermined direction, and an orthodontic device (orthodontic system) having the same. The dental wire supporter includes a limiter having a wire hole into which an orthodontic wire is inserted, and a support base provided at the limiter in order to fix the limiter to a tooth. One side of the wire hole is blocked and an opposite side of the wire hole is open so that the limiter supports the end of the orthodontic wire in a longitudinal direction of the orthodontic wire.

16 Claims, 8 Drawing Sheets

(56) References Cited

U.S. PATENT DOCUMENTS

| | | | | |
|---|---|---|---|---|
| 6,217,324 | B1* | 4/2001 | Kesling | A61C 7/00 433/14 |
| 6,341,956 | B1* | 1/2002 | Liou | A61C 7/12 433/17 |
| 7,713,057 | B2* | 5/2010 | de Salazar Vinas | A61C 7/12 433/17 |
| 8,550,814 | B1* | 10/2013 | Collins | A61C 7/12 433/17 |
| 2003/0170585 | A1* | 9/2003 | Wilkerson | A61C 7/282 433/17 |
| 2004/0197724 | A1* | 10/2004 | Wilkerson | A61C 7/282 433/17 |
| 2005/0244777 | A1* | 11/2005 | Schultz | A61C 7/282 433/17 |
| 2007/0218417 | A1* | 9/2007 | de Salazar Vinas | A61C 7/12 433/17 |
| 2012/0129121 | A1* | 5/2012 | Hwang | A61C 7/282 433/17 |
| 2014/0170585 | A1* | 6/2014 | Parker | A61C 7/22 433/7 |
| 2016/0184067 | A1* | 6/2016 | Parker | A61C 7/12 433/18 |

* cited by examiner

DENTAL WIRE SUPPORTER FOR ORTHODONTIC TREATMENT AND ORTHODONTIC DEVICE HAVING THE SAME

CROSS-REFERENCE TO RELATED APPLICATIONS

This application claims priority to and the benefit of Korean Patent Application No. 10-2015-0035913 filed in the Korean Intellectual Property Office on Mar. 16, 2015, the entire contents of which are incorporated herein by reference.

BACKGROUND OF THE INVENTION

Field of the Invention

The present invention relates to a dental instrument applied to orthodontic treatment, and more particularly, to a dental wire supporter, which is fixed to the teeth so as to support a wire for orthodontic treatment and limits the position of the wire, and an orthodontic device having the same.

Description of the Related Art

For most modern people, look, in particular, appearance has been established as one of standards for judging a person at interviews for employment, admission into a school, etc., and acted as a very important factor in social life, for example, a great part of interpersonal relationship, etc. Particularly, the appearance generally depends on teeth and a set of teeth. Accordingly, orthodontics has recently been prevalent for correcting teeth, a set of teeth or a facial skeleton, along with surgical plastic operation.

The orthodontic treatment is a concept that refers to a treatment of correcting malocclusion, for example, narrow orthodontics of simply strengthening irregular teeth to a nice set of teeth. The orthodontic treatment can correct various skeletal irregularities that may occur during a growth process, thereby contributing to healthy oral organization and further making a beautiful face line to get beautiful impression by changing the anatomical structure of the mouth.

Orthodontic treatment may be categorized into, for example, treatment for gradually moving the set of teeth to improve misaligned teeth or the like odontoparallaxis, growth modification which facilitates or suppresses the growth of the facial skeleton of a patient who is in the period of growth, and orthognathic surgery, which performs a surgical operation on the facial skeleton, more particularly, the jawbone, so as to realize skeletal improvements.

In other words, in the case where treatment by only simple teeth movement is insufficient because of excessive abnormality of the engagement of upper and lower teeth or of the facial skeletal structure, more particularly, the jawbone structure, growth modification may be applied to the jawbone structure during an adolescent period, in which growth is not complete and the abnormality of the jawbone structure is not great, whereas orthognathic surgery, which surgically corrects the abnormality of the jawbone so as to realize a functionally efficient and/or aesthetically pleasing face, may be applied, in combination with other treatments, to the skeletal structure of an adult, the abnormality of which is a medium level or more.

The orthodontic treatment may be broadly classified into labial orthodontics and lingual orthodontics. Here, the labial orthodontics refers to a method of straightening teeth by attaching a brace to a surface of a tooth at a labial side, and the lingual orthodontics refers to a method of straightening teeth by attaching a brace to a surface of a tooth at a lingual side.

As an example of the brace, there are an orthodontic wire, and a wire supporter (generally called a 'bracket') for supporting the orthodontic wire, etc. The bracket is a labial-side and/or a lingual-side of the tooth. A plurality of brackets are provided along a direction of tooth arrangement, and connected by the orthodontic wire, thereby transmitting orthodontic force from the orthodontic wire to the set of teeth.

Orthodontic treatment takes a long time depending on the state of the patient, and there are various kinds of orthodontic treatment including, for example, treatment for alleviating crowding or spacing of the anterior teeth, treatment for reducing protruding lips, and treatment for filling space after the extraction of a tooth or space attributable to tooth loss.

Meanwhile, among the various kinds of orthodontic treatment, orthodontic treatment in which the anterior teeth are moved toward the tongue, that is, the roof of the mouth, is referred to as lingual traction. In the case of the protrusion of teeth in which the teeth of the patient abnormally protrude forward, the lips appear to protrude. Therefore, the above-noted lingual traction has been proposed as one solution for the correction of protruding lips. In addition, in the orthodontic treatment for alleviating the crowding of anterior teeth, the anterior teeth are spread and pulled toward the tongue.

When treatment is advanced in the conventional manner upon administration of the orthodontic treatment described above, because a wire passes through three brackets of posterior teeth as anterior teeth are pulled rearward, friction between one of the three devices (brackets) and the wire is intensified, thus stopping the rearward movement of the anterior teeth and causing lateral movement of the anterior teeth and the posterior teeth. This phenomenon may considerably increase the time required for treatment.

For orthodontic treatment for various purposes as described above, an orthodontic device, which includes, for example, an orthodontic wire configured to suit the treatment purpose and brackets, is installed within the mouth of a patient, and the orthodontic wire is moved simultaneously with the movement of teeth.

SUMMARY OF THE INVENTION

Therefore, the present invention has been made in view of the above problems, and it is an object of the present invention to provide a dental wire supporter, which supports an orthodontic wire and limits the movement of the orthodontic wire in a given direction during the orthodontic treatment, and an orthodontic device (orthodontic system) having the same.

In accordance with an aspect of the present invention, to accomplish the above and other objects, there is provided an orthodontic device, i.e. an orthodontic system including a dental wire supporter for orthodontic treatment, the dental wire supporter including a limiter having a wire hole into which an orthodontic wire is inserted, the wire hole being configured to support one end of the orthodontic wire so as to limit movement of the orthodontic wire, and a support base provided at the limiter in order to be adapted to fix the limiter to a tooth, wherein one side of the wire hole is blocked and an opposite side of the wire hole is open so that the limiter supports the end of the orthodontic wire in a longitudinal direction of the orthodontic wire.

The limiter may include a support body, through which the wire hole is formed so that the orthodontic wire is inserted into the support body, and a stopper provided at the support body so as to block one side of the wire hole.

The stopper may include a hole cover provided at one side of the support body. The hole cover can be provided at the support body to selectively open the one side of the support body.

The stopper can be assembled to the support body so as to block one side of the wire hole. And the limiter can be in the shape of a tube, one side of which is blocked.

The orthodontic device comprising an arch wire having an arch shape so as to be adapted to be provided along a set of anterior teeth, an anterior bracket adapted to be fixed to each of incisors in order to couple the arch wire to the anterior teeth, the anterior bracket supporting the arch wire, guide brackets provided on both sides of the arch wire so as to be adapted to be fixed to one of left molars and one of right molars, respectively, the guide brackets supporting both sides of the arch wire so as to guide rearward movement of the arch wire, the arch wire slidably passing through the guide brackets, a canine bracket provided between the anterior bracket and each of the guide brackets so as to be adapted to be fixed to each of both canines, the canine bracket supporting the arch wire at a position in front of each of the guide brackets, a guide wire provided on either side of the arch wire so as to be adapted to guide rearward movement of the anterior teeth and supported by each of the guide brackets, the guide wire slidably passing through the canine bracket, wire supporters provided at a rear of the guide brackets so as to be adapted to be fixed to another one of the left molars and another one of the right molars, respectively, each of the wire supports supporting a rear end of the guide wire so as to limit rearward movement of the guide wire, and a traction member configured to provide the arch wire with traction force for the rearward movement of the anterior teeth.

The canine bracket may include a first canine bracket configured to support the arch wire, and a second canine bracket configured to slidably support the guide wire.

Each of the guide brackets may include a first supporter configured to support the guide wire, and a second supporter configured to slidably support the arch wire.

The first supporter can be integrated with the second supporter. And each of the guide brackets may further include a bendable connector connecting the first supporter and the second supporter.

One of the first supporter and the second supporter may include a bracket base adapted to fix the guide bracket to a tooth.

Each of the guide brackets may further include a rear holder for connection of the traction member. The arch wire may include a front holder for connection of the traction member.

The anterior bracket can be integrated with the arch wire, or movably provided on the arch wire.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
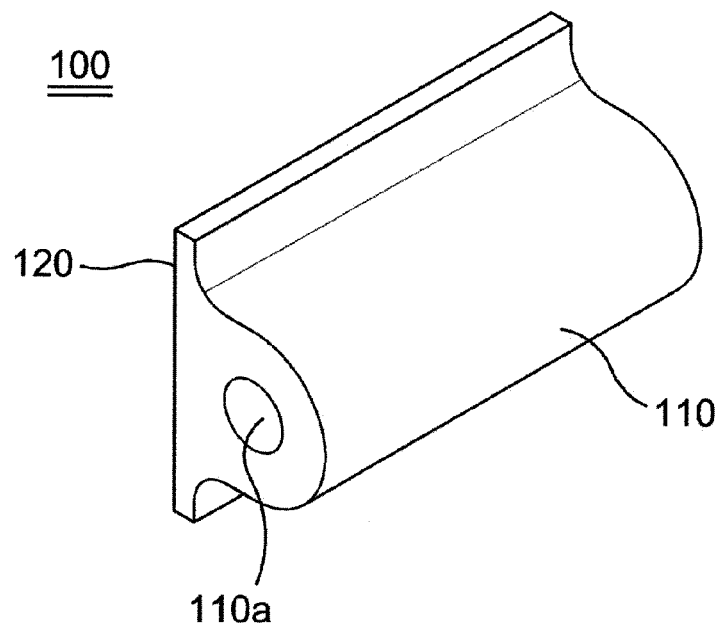
FIG. 1 is a perspective view illustrating one embodiment of a dental wire supporter in accordance with the present invention.

Hereinafter, exemplary embodiments of the present invention, which may concretely realize the object of the present invention, will be described with reference to the accompanying drawings. In the description of the embodiments, the same constituent element is designated by the same name and the same reference numeral, and a repeated description thereof is omitted hereinafter.

First, with reference to FIGS. 1 to 4, one embodiment of a dental wire supporter in accordance with the present invention will be described below.

Figure 2:
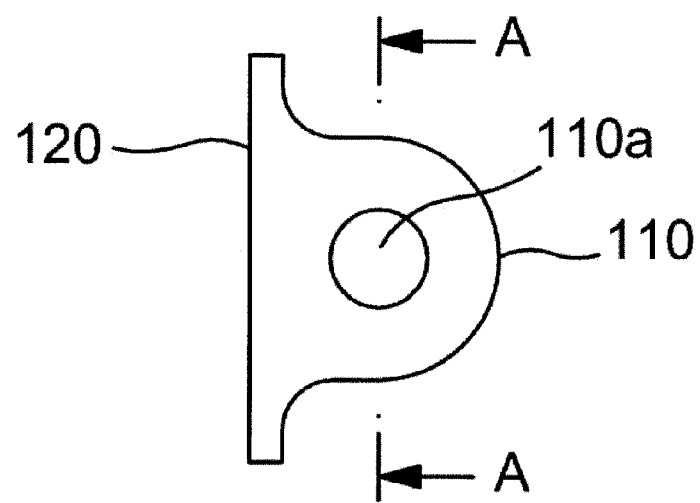
FIG. 2 is a side view of the dental wire supporter illustrated in FIG. 1.
Figure 3:
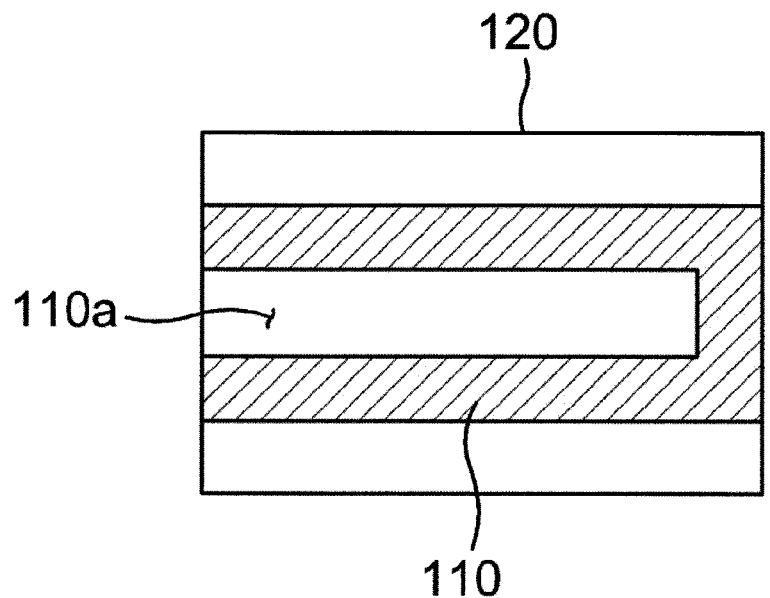
FIG. 3 is a sectional view taken along line A-A of FIG. 2.
Figure 4:
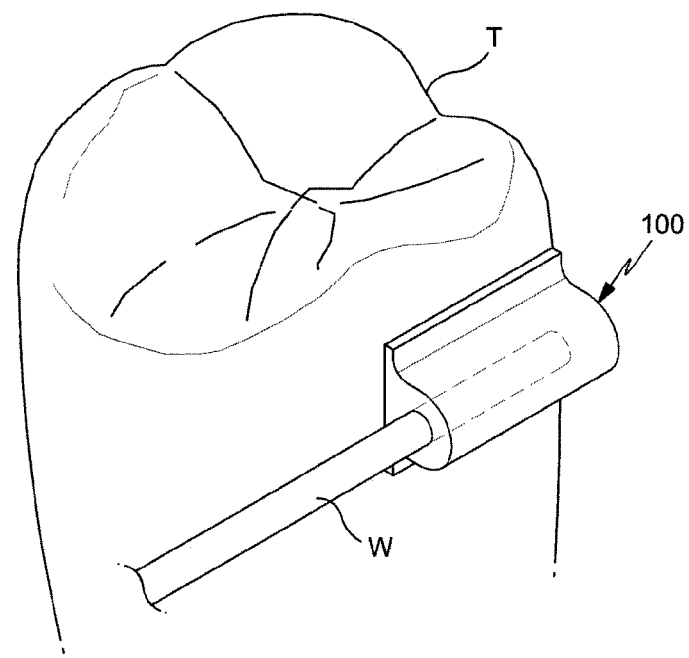
FIG. 4 is a perspective view illustrating the state in which the dental wire supporter of FIG. 1 is applied to a tooth.

Among the accompanied drawings, FIG. 1 is a perspective view illustrating one embodiment of a dental wire supporter in accordance with the present invention, FIG. 2 is a side view of the dental wire supporter illustrated in FIG. 1, FIG. 3 is a sectional view taken along line A-A of FIG. 2, and FIG. 4 is a perspective view illustrating the state in which the dental wire supporter of FIG. 1 is applied to a tooth.

The present invention relates to a wire supporting structure for orthodontic treatment, i.e. an orthodontic bracket and orthodontic device having the same.

Referring to FIGS. 1 to 4, the dental wire supporter in accordance with one embodiment of the present invention, which is designated by reference numeral 100, is used in orthodontic treatment in order to support an orthodontic wire W, which is installed inside the mouth. In particular, the dental wire supporter 100 defines the movement limit of the wire W, thereby preventing the wire W from being pushed.

Accordingly, the dental wire supporter 100 may be referred to as a limit bracket or stop bracket, which supports the wire W and limits the movement of the wire W.

The dental wire supporter 100 comprises a limiter 110 and a support base 120. The limiter 110 is provided with a wire hole 110a so that the orthodontic wire W is inserted into the wire hole 110a.

More specifically, the wire hole 110a is formed in the limiter 110 and serves to support one end of the orthodontic wire W so as to limit the movement of the orthodontic wire W. In other words, the wire hole 110a is shaped such that one side thereof is blocked and the opposite side thereof is open, in order to support one end of the orthodontic wire W in the longitudinal direction of the orthodontic wire W.

The limiter 110 serves to support one end of the orthodontic wire W so as to prevent the orthodontic wire W from being pushed in a given direction. In the present embodiment, the blocked side of the wire hole 110a blocks one end of the wire W and the opposite open side of the wire hole 110a forms the inlet of the wire hole 110a.

In addition, the support base 120 is provided at the limiter 110. The support base 120 is an element adapted to fix the limiter 110 to a tooth T. More specifically, the support base 120 is provided on one side of the limiter 110 and is mechanically or chemically fixed to the tooth T.

In the present embodiment, the support base 120 is attached to the surface of the tooth T using an adhesive. To this end, the support base 120 has a tooth adhesion surface.

In addition, although the limiter 110 takes the form of a tube, one side (the left side or the right side) of which is blocked, the external shape of the tube is not limited, and the cross section of the limiter 110, which is perpendicular to the wire hole 110a, may have any of various shapes, such as, for example, a circular or square shape. As such, the wire hole 110a may also have a circular or square shape.

In addition, the limiter 110 and the support base 120 may be integrally formed with each other using the same material, and, for example, may be manufactured using a metal or dental resin that is compatible for use inside the mouth.

The wire supporter 100 may be manufactured to be personalized for a patient using three-dimensional (3D) modeling, for example 3D printing, to suit the shape of the surface of a tooth based on patient's mouth image data, or may be manufactured using processing equipment or a mold. For reference, FIG. 4 is a view illustrating the state in which the wire supporter 100 is fixed to a molar T and one exemplary orthodontic wire W is inserted into the wire supporter 100.

Meanwhile, the limiter 110 may include a support body 111, through which the wire hole 110a is formed so that both ends of the support body 111 are open, in order to enable the insertion of the orthodontic wire W, and a stopper 112, 113 or 114 provided at the support body 111 to block one side of the wire hole 110a.

The stopper 112, 113 or 114 serves to block one side of the support body 111, more specifically, the rear side of the support body 111. The stopper 112, 113 or 144 may be configured into various shapes so that it is inserted into an opening in one side of the support body 111, or covers one side of the support body 111, for example. More specifically, the limiter 110 may include a cover-type stopper, i.e. a hole cover, which is coupled to one side of the support body 111.

Figure 5:
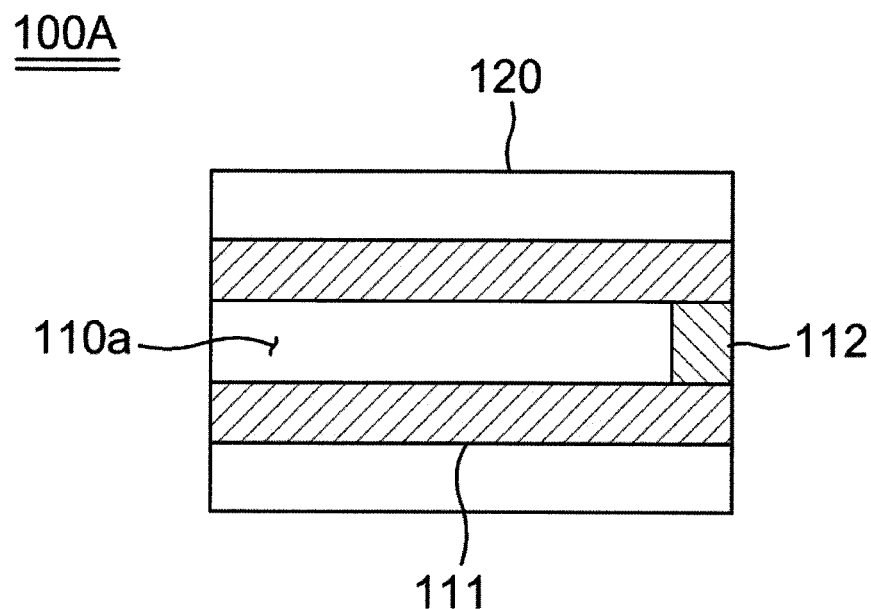
FIG. 5 is a sectional view illustrating another embodiment of a dental wire supporter in accordance with the present invention.
Figure 6:
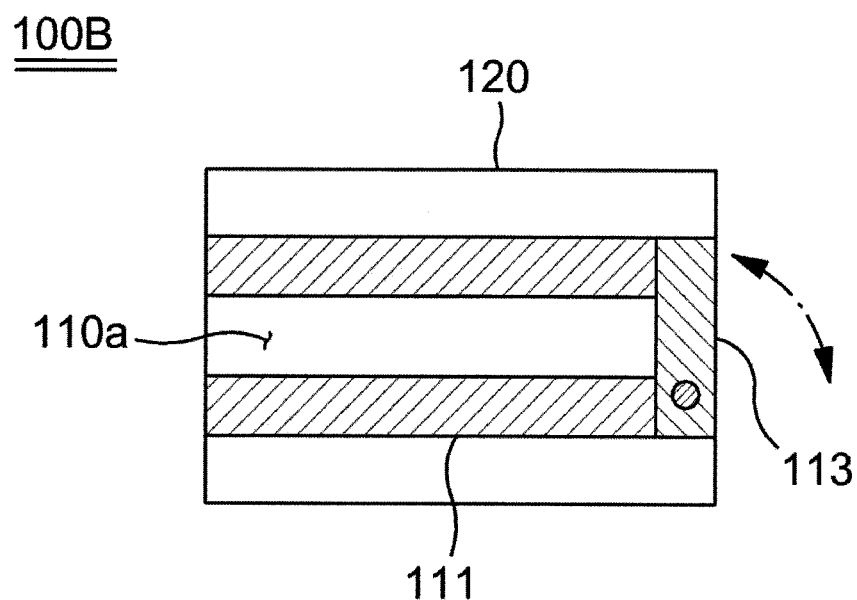
FIG. 6 is a sectional view illustrating another embodiment of a dental wire supporter in accordance with the present invention.
Figure 7:
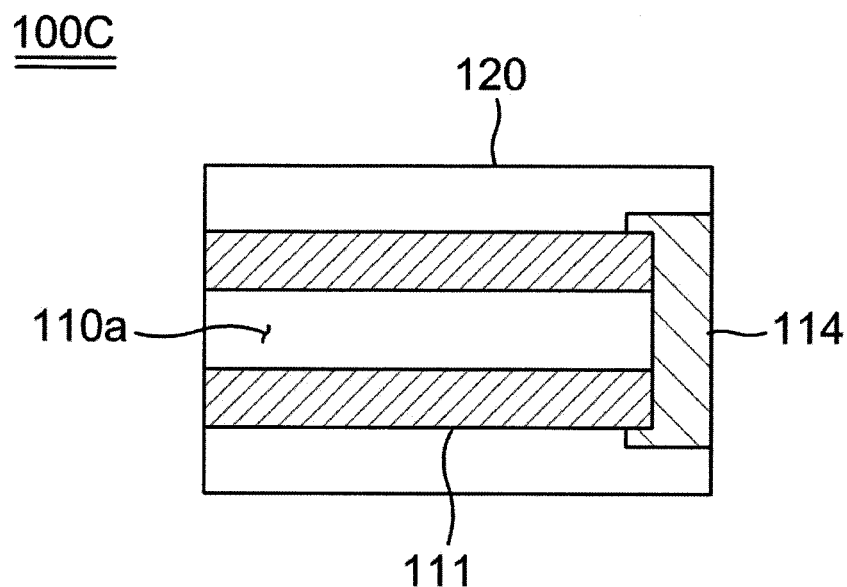
FIG. 7 is a sectional view illustrating another embodiment of a dental wire supporter in accordance with the present invention.

In another embodiment illustrated in FIG. 5 (i.e. a second embodiment 110A), the stopper 112, which is configured so as to be inserted into an opening in one side of the support body 111, may be applied to the support body 111. In other embodiments illustrated in FIGS. 6 and 7 (i.e. a third embodiment 100B and a fourth embodiment 100C), the stopper 113 or 114, which is configured so as to cover one side opening of the support body 111, may be applied to the support body 111.

In the embodiments of the present invention, the stopper 112, 113 or 114 may be formed of the same material as the support body 111, or may be formed of a different material, for example, rubber. The stopper 112, 113 or 114 may limit the movement, i.e. sliding of the wire W by closing one side of the support body 111.

In addition, the stopper, i.e. the hole cover, may be assembled to the support body 111 so as to block one side of the wire hole 110a, and may be opened away from or closed to the support body 111. The stopper 113 of the third embodiment 100B is configured to selectively close one side of the support body 111 via rotation thereof, and the stopper 114 of the fourth embodiment 100C takes the form of a cap that is fitted to one side of the support body 111.

Figure 8:
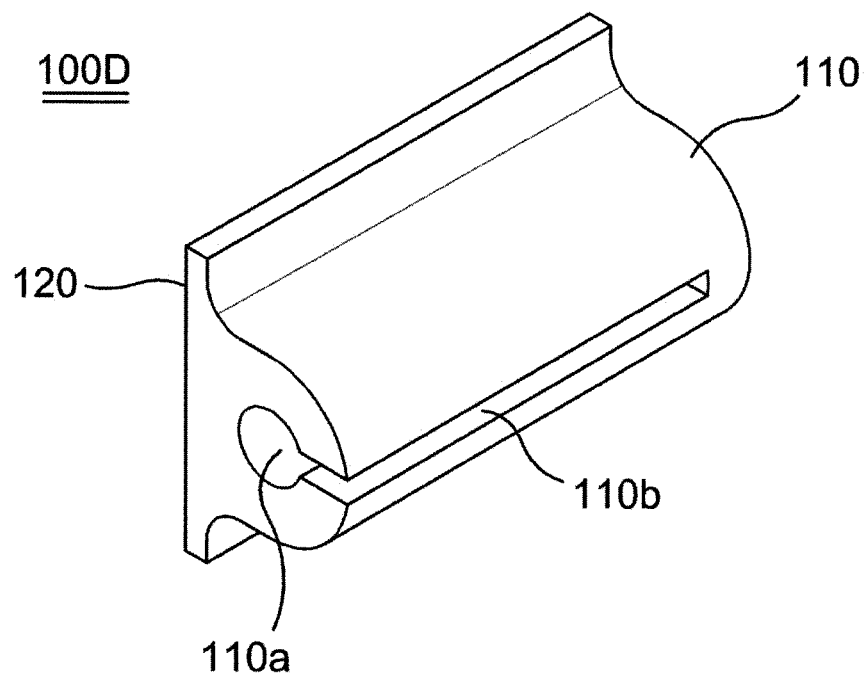
FIG. 8 is a sectional view illustrating a further embodiment of a dental wire supporter in accordance with the present invention.

Meanwhile, the limiter 110 may have a slot 100b formed in the peripheral wall surface thereof as illustrated in FIG. 8. In other words, the limiter 110 is not limited to the configuration having the completely closed periphery. Detailed examples of application of the dental wire supporter described above will be described in relation to one embodiment of an orthodontic device.

Next, another example of an orthodontic bracket for an orthodontic device in accordance with the present invention will be described with reference to FIGS. 9 to 11.

Figure 9:
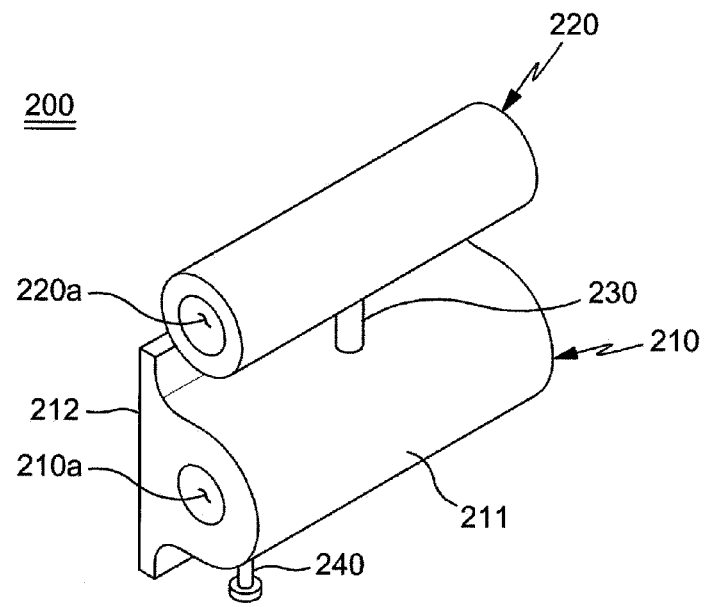
FIG. 9 is a perspective view illustrating one embodiment of a guide bracket, which may be applied to an orthodontic device, in accordance with the present invention.
Figure 10:
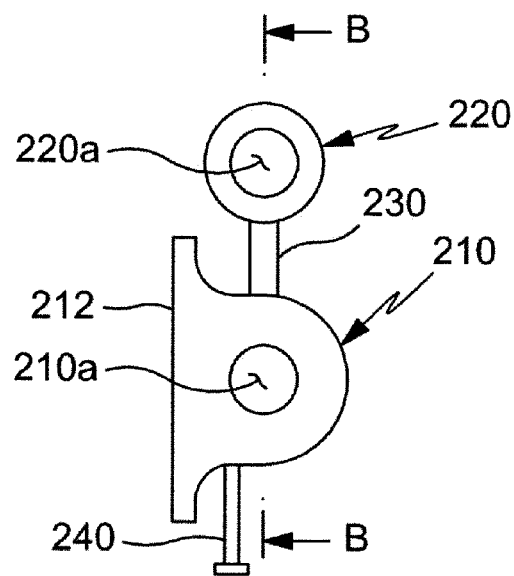
FIG. 10 is a side view of the guide bracket illustrated in FIG. 9.
Figure 11:
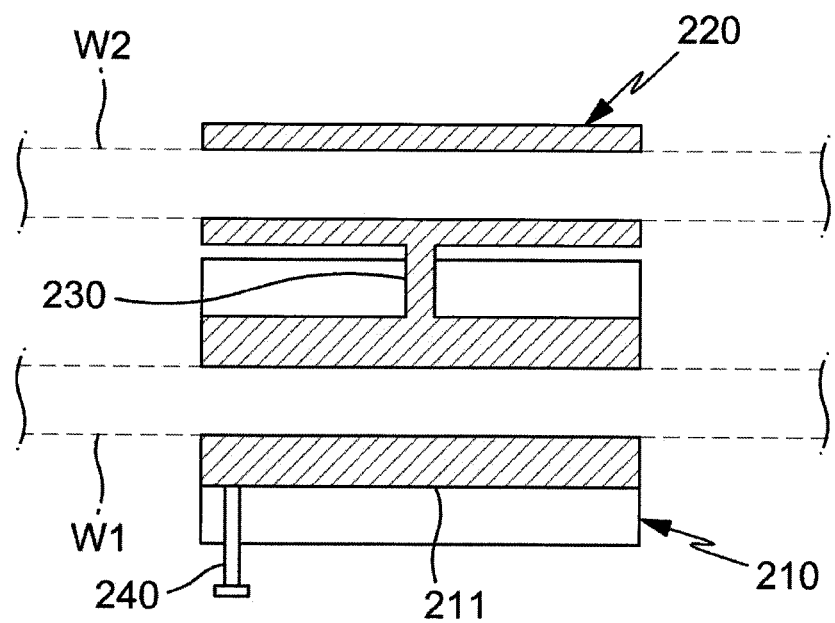
FIG. 11 is a sectional view taken along line B-B of FIG. 10.

Referring to FIGS. 9 to 11, the orthodontic bracket in accordance with another embodiment of the present invention, which is designated by reference numeral 200, is a bracket capable of supporting a plurality of wires. In the present invention, for convenience of description, the orthodontic bracket is referred to as a guide bracket 200.

The guide bracket 200 is comprised of a first supporter 210 and a second supporter 220, which support separate wires W1 and W2 respectively. More specifically, the first supporter 210 and the second supporter 220 respectively have a first wire hole 210a and a second wire hole 220a, which have openings in both side thereof.

Wires, which have specifications suitable for treatment purposes, may be slidably inserted into, or may be interference-fitted, into the first supporter 210 and the second supporter 220. For convenience of description, the wire mounted in the first supporter 210 may be referred to as a first wire W1, and the wire mounted in the second supporter 220 may be referred to as a second wire W2. The first wire W1 and the second wire W2 may have different thicknesses or cross-sectional shapes so as to realize the orthodontic effects desired by the operator.

In addition, the first supporter 210 and the second supporter 220 are connected to each other. For example, the first supporter 210 and the second supporter 220 may be connected to each other via a connector 230. The connector 230 may be bendable. As such, because any one of the first supporter 210 and the second supporter 220 may be adjusted in position or direction on the basis of the other one, the freedom in the installation of the orthodontic wires may be increased.

In the present embodiment, the first supporter 210 and the second supporter 220 are integrally formed with each other. That is, the first supporter 210 and the second supporter 220 are integrally formed with each other with the connector 230 interposed therebetween.

As described above, when the first supporter 210 and the second supporter 220 are connected to each other, both of the supporters 210 and 220 may be installed within the mouth even if only one of the first supporter 210 and the second supporter 220 is fixed to a tooth.

To this end, one of the first supporter 210 and the second supporter 220 includes a bracket base 212 adapted to fix the guide bracket 200 to the tooth. Although the bracket base 212 of the present embodiment is provided on the first supporter 210, the embodiment is not limited thereto, and the bracket base 212 may be provided on the second supporter 220.

More specifically, the first supporter 210 of the present embodiment includes a tube body 211 having a first wire hole 210a, and the bracket base 212, which is configured to fix the tube body 211 to the surface of the tooth.

The bracket base 212 may be mechanically or chemically fixed to the surface of the tooth. In the present embodiment, the bracket base 212 has a tooth adhesion surface so as to be attached to the surface of the tooth using a dental adhesive.

In the present embodiment, although the first supporter 210 and the second supporter 220 is in the shape of a tube, both sides of which are open, the external shape of the tube is not limited thereto and the tube may have a circular or square cross-sectional shape. Additionally, the shape of the first wire hole 210a and the second wire hole 220a is not limited to a circular shape.

In addition, the guide bracket 200 may further include a holder 240 or a hook for the connection of a traction member which is formed of an elastic material, such as, for example, a rubber string or a spring. The holder 240 is formed on one side of the guide bracket 200. More specifically, the holder 240 is provided on the first supporter 210 and/or the second supporter 220. In the present embodiment, the holder 240 protrudes from the first supporter 210. The holder 240 may have any of various shapes such as, for example, a looped hook or a T-shaped or L-shaped member, and may be applied to the dental wire supporters 100 to 100D described above.

The guide bracket 200 may be manufactured using a metal or dental resin that is compatible for use inside the mouth. In addition, the guide bracket 200 may be manufactured to be personalized for a patient using three-dimensional (3D) modeling, for example 3D printing, to suit the shape of the surface of a tooth based on patient's mouth image data, or may be manufactured using processing equipment or a mold.

Figure 12:
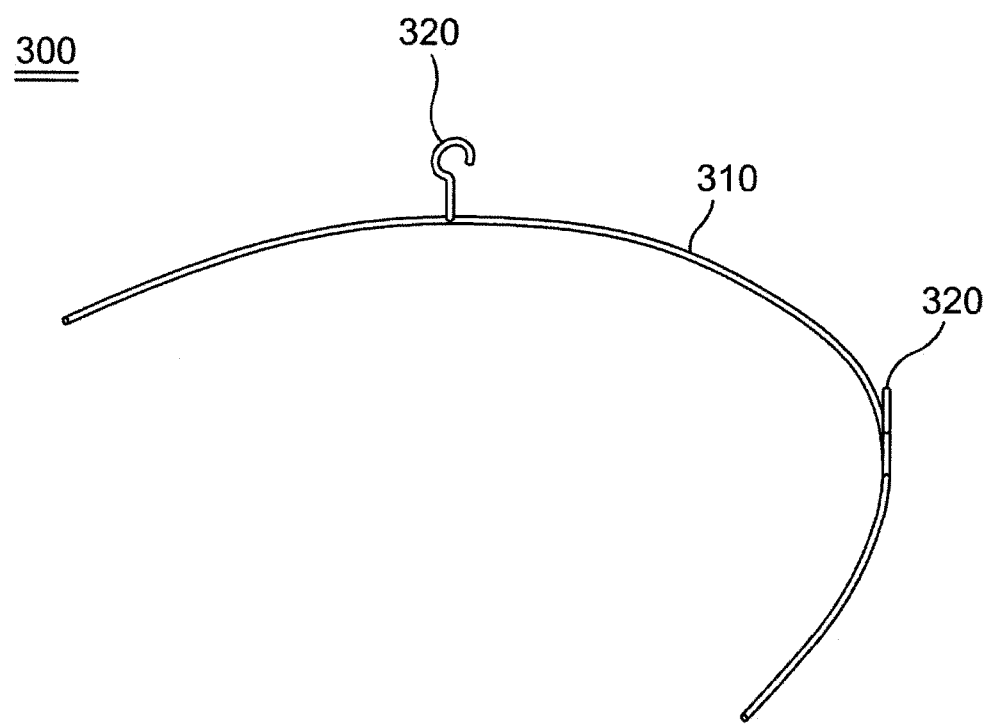
FIG. 12 is a perspective view illustrating one embodiment of an arch wire by way of example of an orthodontic wire, which may be applied to the orthodontic device in accordance with the present invention.

Meanwhile, FIG. 12 is a view illustrating one example 300 of an orthodontic wire of an orthodontic device, i.e. an orthodontic system in accordance with the present invention. One example 300 of the wire includes an arch wire 310, which has an arch shape and is provided along the set of anterior teeth. The arch wire 310 is attached to the lingual side or labial side of the anterior teeth via the orthodontic bracket.

In other words, orthodontic brackets are fixed to respective anterior teeth (incisors and canines), and the arch wire 310 is inserted into the orthodontic brackets, and more specifically anterior brackets, which are fixed to the left and right incisors, so as to realize the movement of the anterior teeth.

Figure 13:
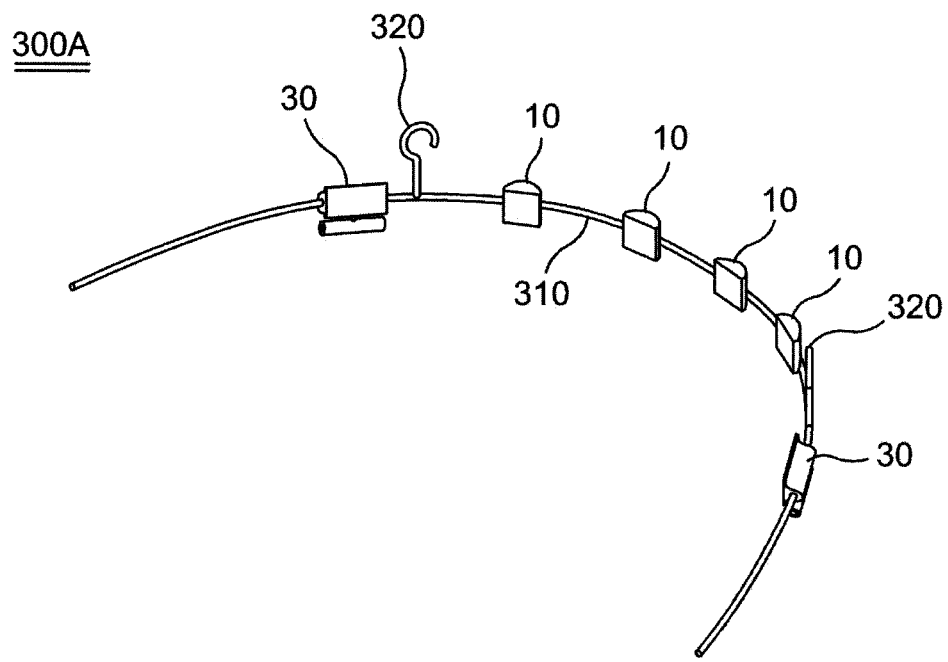
FIG. 13 is a perspective view illustrating the state in which tooth brackets are connected to the arch wire illustrated in FIG. 12.
Figure 14:
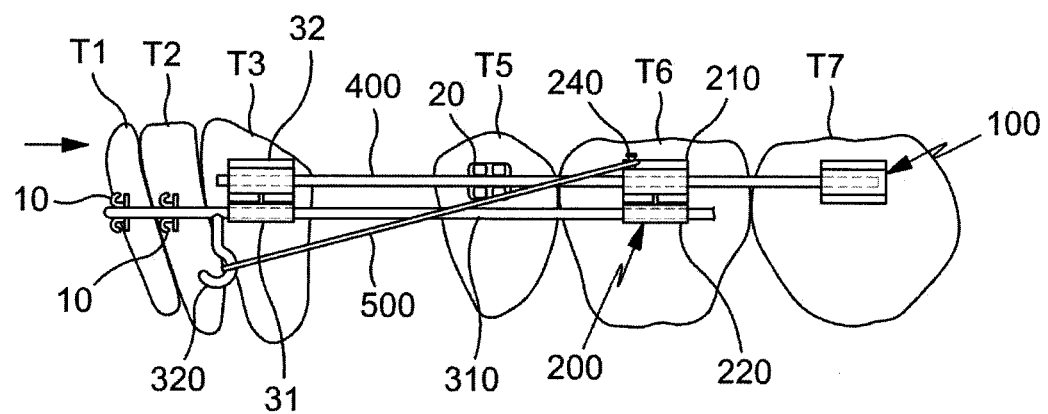
FIG. 14 is a side view illustrating the state in which the orthodontic device in accordance with the present invention is installed on the teeth.
Figure 15:
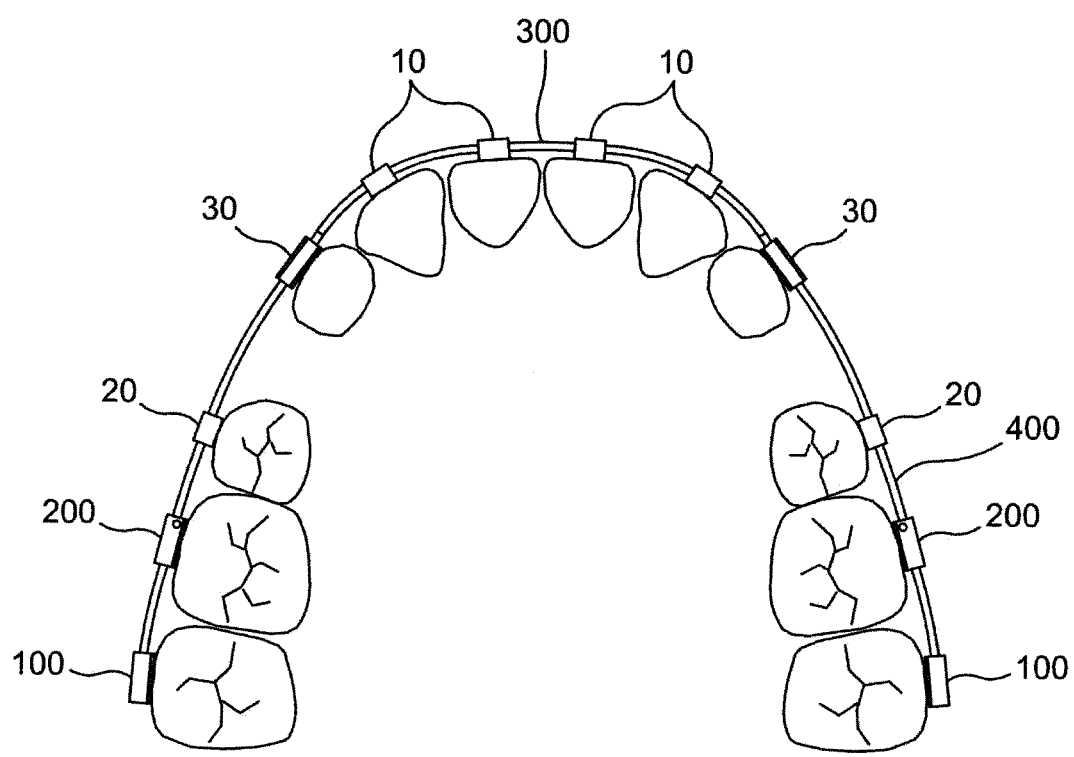
FIG. 15 is a plan view of FIG. 14.

Because examples of anterior brackets having various configurations in which a slot-shaped wire coupling groove is formed for the mounting of an orthodontic wire are known, an additional description thereto is omitted herein. FIG. 13 is a perspective view illustrating the state in which the arch wire illustrated in FIG. 12 is connected to tooth brackets, and more particularly, to anterior brackets.

Referring to FIGS. 12 and 13, the arch wire 310 may include a hook or a holder 320 for the connection of a traction member formed of an elastic material. In the present embodiment, although a looped hook is disclosed as the wire holder 320, the shape of the holder 320 is not limited thereto, and two holders may respectively be provided in a left portion and a right portion of the arch wire 310.

Anterior brackets 10 are structures that are fixed to the left and right incisors in order to couple the arch wire 310 to the anterior teeth. The anterior brackets 10 support the arch wire 310 and transmit the force applied from the arch wire 310 to the anterior teeth.

The anterior brackets 10 may be fixed to the arch wire 310 at given positions. The anterior brackets 10 are positioned and fixed so as to be spaced apart from each other in the longitudinal direction of the arch wire 310. For example, the anterior brackets 10 may be fixed in place on the arch wire 310 via soldering, and may be attached to the lingual surfaces or labial surfaces of the anterior teeth using a dental adhesive. Paste for soldering, i.e. soldering paste may be silver solder, without being limited thereto. The present embodiment discloses labial orthodontics in which the anterior brackets 10 are fixed to the labial surfaces of the anterior teeth, i.e. the labial surfaces of the left and right incisors.

Of course, the anterior brackets 10 may be movable along the arch wire 310. When the anterior brackets 10 are movably provided on the arch wire 310, the positions of the anterior brackets 10 may be adjusted to suit the set of the anterior teeth.

In addition, canine brackets 30, which is adapted to couple the arch wire 310 to the left and right canines, may also be mounted to the arch wire 310 to realize the orthodontic device.

Hereinafter, a detailed example of the orthodontic device in accordance with the present invention will be with reference to FIGS. 12 to 15.

The orthodontic device in accordance with one embodiment of the present invention is a system for tracking anterior teeth T1, T2 and T3 rearward, and includes the arch wire 310, the anterior brackets 10, the guide brackets 200, the canine bracket 30, the guide wire 400, and the dental wire supporters 100. In addition, a tracking member 500, which is formed of an elastic material, such as, for example, a rubber string or a spring, is applied for the traction of the arch wire 310.

The arch wire 310 has an arch shape so as to be provided along the set of anterior teeth. The anterior brackets 10 may be fixed to the incisors in order to mount the arch wire 310 to the anterior teeth T1, T2 and T3, and serve to support the arch wire 310. Generally, the anterior teeth mean teeth corresponding to the central incisor, the lateral incisors, and the canines.

The guide brackets 200 are provided on both side of the arch wire 310 so as to be fixed to one of the left molars and one of the right molars, respectively. The guide bracket 200 supports either side of the arch wire 310 so as to guide the rearward movement of the arch wire 310. In the present embodiment, the arch wire 310 slidably penetrates, i.e. passes through the guide bracket 200, and the guide bracket 200 is fixed to the buccal side of a tooth No. 6 (first molar).

The canine bracket 30 is provided between the anterior bracket 10 and the guide bracket 200 so as to be fixed to each of both canines of a patient, and supports the arch wire 310 at a position in front of each of the guide brackets 200.

Next, the guide wire 400 extends in rear directions of the arch wire 310 at either side of the arch wire 310 so as to guide the rearward movement of the anterior teeth. As such, the guide wire 400 overlaps the either side of the arch wire 310.

The guide wire 400 passes through the guide bracket 200 and is slidably supported by the canine bracket 30. More specifically, the guide wire 400 slidably penetrates the canine bracket 30.

In addition, each of the wire supporters 100 is provided at the rear of the guide bracket 200, and supports the rear portion of the guide wire 400 to thereby limit the rearward movement of the guide wire 400.

Each of the wire supporters 100 is fixed to the surface of another tooth of the left molars and another tooth of the right molars, excluding the tooth to which the guide bracket is installed, for example, a tooth No. 7 (second molar).

The canine bracket 30 includes a first canine bracket 31 and a second canine bracket 32. The arch wire 310 is inserted into any one of the first canine bracket 31 and the second canine bracket 32, and the guide wire 400 is inserted into the other one. In the present embodiment, the part of the canine bracket 30 into which the arch wire 310 is inserted is referred to as the first canine bracket 31, and the part of the canine bracket 30 into which the guide wire 400 is inserted is referred to as the second canine bracket 32.

The guide wire 400 slidably penetrates the second canine bracket 32, and consequently, is slidably supported by the second canine bracket 32.

The first canine bracket 31 and the second canine bracket 32 may be connected to each other, or may be separately provided without being connected. In the present embodiment, the first canine bracket 31 and the second canine bracket 32 are connected to each other, and the canine bracket 30 may take the form of a pair of tubes connected to each other in the same manner as the guide bracket 200 described above.

In addition, the arch wire 310 is inserted into any one of the first supporter 210 and the second supporter 220 of the guide bracket 200, and the guide wire 400 is inserted into the other one.

In the present embodiment, the guide wire 400 is inserted into the first supporter 210 and the arch wire 310 is inserted into the second supporter 220, but the opposite configuration is of course also possible. For convenience of description, the part into which the guide wire 400 is inserted may be referred to as a first supporter.

The guide wire 400 passes through the first supporter 210 and is slidably inserted into the second canine bracket 32 as described above, and the arch wire 310 penetrates the first canine bracket 31 and is slidably inserted into the second supporter 220.

Meanwhile, the traction member 500 serves to provide the arch wire 310 with traction force for the rearward movement of the anterior teeth T1, T2 and T3. One end (the front portion) of the traction member 500 is connected to the holder (the front holder) 320 of the arch wire 310, and the other end (the rear portion) of the traction member 500 is connected to the holder (the rear holder) 240 of the guide bracket 200. Of course, the front portion of the traction member 500 may be directly connected to the anterior bracket 10 or the arch wire 310.

Reference numeral 20, not described above, is a bracket that supports the guide wire 400 at a position in front of the guide bracket 200. The bracket 20 may assist the integrated behavior of the molars, and may be a known molar bracket having a slot-shaped wire coupling groove or a tube-shaped bracket.

With the orthodontic device described above, i.e. an orthodontic system that realizes the rearward movement of the anterior teeth, friction applied to the orthodontic wires (the arch wire and the guide wire) during the traction of the anterior teeth may be reduced, which may prevent tilting of the teeth during orthodontic treatment and prevent soft tissues inside the mouth from being damaged by the wires.

In addition, when the anterior teeth T1, T2 and T3 are gradually moved rearward by the traction member 500 as described above, the canine bracket 30 is also moved rearward. At this time, because the rear end of the guide wire 400 is supported and pushed forward by the dental wire supporter 100, when the anterior teeth T1, T2 and T3 are moved rearward, the tip end of the guide wire 400 gradually protrudes forward from the canine bracket 30.

In this process, the guide wire 400 guides the rearward movement of the anterior teeth T1, T2 and T3, and provides the anterior teeth T1, T2 and T3 with reaction force against the traction member 500 so as to prevent tilting of the teeth. Simultaneously, either end of the arch wire 310 is introduced through the guide bracket 200, more particularly, through the second supporter 220 from the rear end of the guide bracket.

In addition, as the operator cuts either end of the arch wire 310 and the tip end of the guide wire 400 by the same length as the moved distance of the anterior teeth, it is possible to prevent damage to soft tissues and the generation of infection. In addition, either end of the arch wire 310 and the tip end of the guide wire 400 are exposed to a portion to which a dental cutter is easily accessible, which may facilitate the operation by the operator and decrease the discomfort of the patient.

Although the orthodontic device described in the present embodiment is a labial orthodontic device installed to the lower teeth, it is to be noted that the orthodontic device may also be applied to orthodontia of the upper teeth.

The exemplary embodiments of the present invention have been described above, and it is clear to those skilled in the art that the present invention may be embodied into other specific forms other than the above-described embodiments without departing from the purpose or scope of the present invention.

Accordingly, the scope of the present invention should not be limited to and defined by the above-described embodiments, and the invention is to cover all modifications, equivalents, and alternatives falling within the spirit and scope of the invention as defined by the claims.

A dental wire supporter and an orthodontic device having the same in accordance with the present invention may have the following technical effects.

First, the present invention may prevent damage to soft tissues inside the mouth and infection thereof attributable to the movement of an orthodontic wire simultaneously with the movement of teeth, thereby decreasing the discomfort experienced by a patent during the progress of treatment.

Second, because the front end (tip end) of a rear orthodontic wire (i.e. a guide wire) penetrates only a tube of the canine and the rear end of a front orthodontic wire (i.e. an arch wire) penetrates only a tube of the second molar, the present invention may remarkably reduce friction compared to a conventional treatment in which a single steel wire passes through square bracket slots (wire coupling grooves) of three molars, and may achieve a considerable reduction in treatment duration by reducing unnecessary tooth movement, such as tilting of the teeth, compared to the use of two steel wires.

Third, by limiting the movement of the orthodontic wire, the present invention may prevent the rearward movement of the wire during orthodontic treatment that involves the rearward movement of anterior teeth, thereby improving the ease of handling of the wire and the accessibility of a distal end cutter, and realizing an orthodontic device, i.e. an orthodontic system, which may facilitate cutting of the wire to be appropriate for the position to which it is desired to move the anterior teeth.

Fourth, the present invention may realize the indentation or extrusion of posterior teeth simultaneously with the rearward movement of anterior teeth, may prevent the tilting of teeth during the progress of orthodontic treatment, and may realize an orthodontic system having low friction resistance.

Fifth, the present invention may enable the easy construction (installation) of an orthodontic system for orthodontic treatment within the mouth, thereby effectively guiding the movement of anterior teeth and easy treatment, and rapidly achieving the desired orthodontic effects.

What is claimed is:

1. An orthodontic device comprising:
   an arch wire having an arch shape so as to be adapted to be provided along a set of anterior teeth;
   an anterior bracket adapted to be fixed to each of incisors in order to couple the arch wire to the anterior teeth, the anterior bracket supporting the arch wire;
   guide brackets provided on both end portions of the arch wire so as to be adapted to be fixed to one of left molars and one of right molars, respectively, the guide brackets supporting the end portions of the arch wire so as to guide rearward movement of the arch wire, the arch wire slidably passing through the guide brackets;
   a canine bracket provided between the anterior bracket and each of the guide brackets so as to be adapted to be fixed to each of both canines, the canine bracket supporting the arch wire at a position in front of each of the guide brackets;
   a guide wire provided on either portion of the arch wire so as to be adapted to guide rearward movement of the anterior teeth and supported by each of the guide brackets, the guide wire slidably passing through the canine bracket;
   wire supporters provided at a rear of the guide brackets so as to be adapted to be fixed to another one of the left molars and another one of the right molars, respectively, each of the wire supporters supporting a rear end of the guide wire so as to limit rearward movement of the guide wire; and
   a traction member configured to provide the arch wire with traction force for the rearward movement of the anterior teeth.

2. The orthodontic device according to claim 1, wherein the canine bracket includes:
   a first canine bracket portion configured to support the arch wire; and
   a second canine bracket portion configured to slidably support the guide wire.

3. The orthodontic device according to claim 1, wherein each of the guide brackets includes:
   a first supporter configured to support the guide wire; and
   a second supporter configured to slidably support the arch wire.

4. The orthodontic device according to claim 3, wherein the first supporter is integrated with the second supporter.

5. The orthodontic device according to claim 4, wherein each of the guide brackets further includes a bendable connector connecting the first supporter and the second supporter.

6. The orthodontic device according to claim 5, wherein one of the first supporter and the second supporter includes a bracket base adapted to fix the guide bracket to a tooth.

7. The orthodontic device according to claim 4, wherein one of the first supporter and the second supporter includes a bracket base adapted to fix the guide bracket to a tooth.

8. The orthodontic device according to claim 4, wherein each of the guide brackets further includes a rear holder for connection of the traction member.

9. The orthodontic device according to claim 1, wherein the arch wire includes a front holder for connection of the traction member.

10. The orthodontic device according to claim 1, wherein the anterior bracket is integrated with the arch wire, or is movably provided on the arch wire.

11. The orthodontic device according to claim 1, wherein each of the wire supporters comprises:
    a limiter having a wire hole into which the guide wire is inserted, the wire hole being configured to support the rear end of the guide wire so as to limit movement of the guide wire; and
    a support base provided at the limiter, the support base being adapted to fix the limiter to a tooth to which each wire supporter is adapted to be fixed,
    wherein a rear side of the wire hole is blocked and a front side of the wire hole is open so that the limiter supports the rear end of the guide wire in a longitudinal direction of the guide wire.

12. The orthodontic device according to claim 11, wherein the limiter includes:
    a support body, through which the wire hole is formed so that the guide wire is inserted into the support body; and
    a stopper provided at the support body so as to block the rear side of the wire hole.

13. The orthodontic device according to claim 12, wherein the stopper includes a hole cover provided at a rear side of the support body.

14. The orthodontic device according to claim 13, wherein the hole cover is provided at the support body to selectively open the rear side of the support body.

15. The orthodontic device according to claim 12, wherein the stopper is assembled to the support body so as to block the rear side of the wire hole.

16. The orthodontic device according to claim 11, wherein the limiter is in the shape of a tube, a rear side of which is blocked.

* * * * *